US012077590B2

(12) United States Patent
Davila

(10) Patent No.: US 12,077,590 B2
(45) Date of Patent: Sep. 3, 2024

(54) BISPECIFIC ANTIBODY FOR CANCER IMMUNOTHERAPY

(71) Applicant: H. LEE MOFFITT CANCER CENTER AND RESEARCH INSTITUTE, INC., Tampa, FL (US)

(72) Inventor: Marco L. Davila, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 878 days.

(21) Appl. No.: 16/487,372

(22) PCT Filed: Feb. 22, 2018

(86) PCT No.: PCT/US2018/019181
§ 371 (c)(1),
(2) Date: Aug. 20, 2019

(87) PCT Pub. No.: WO2018/156735
PCT Pub. Date: Aug. 30, 2018

(65) Prior Publication Data
US 2020/0181260 A1  Jun. 11, 2020

Related U.S. Application Data

(60) Provisional application No. 62/462,057, filed on Feb. 22, 2017.

(51) Int. Cl.
*C07K 16/28* (2006.01)
(52) U.S. Cl.
CPC ...... *C07K 16/283* (2013.01); *C07K 2317/622* (2013.01)
(58) Field of Classification Search
None
See application file for complete search history.

(56) References Cited

U.S. PATENT DOCUMENTS

| | | | |
|---|---|---|---|
| 5,579,250 A | 11/1996 | Balaji et al. | |
| 5,612,895 A | 3/1997 | Balaj et al. | |
| 5,631,280 A | 5/1997 | Ciccarone et al. | |
| 8,008,449 B2 | 8/2011 | Korman et al. | |
| 8,552,154 B2 | 10/2013 | Freeman et al. | |
| 8,617,546 B2 | 12/2013 | Kang et al. | |
| 8,847,356 B2 | 9/2014 | Saita et al. | |
| 9,493,578 B2* | 11/2016 | Lazar | C07K 16/2809 |
| 2004/0058447 A1 | 3/2004 | Ueno et al. | |
| 2004/0101519 A1 | 5/2004 | June et al. | |
| 2006/0233787 A1* | 10/2006 | Le Gall | C07K 16/2809 |
| | | | 435/327 |
| 2009/0092589 A1 | 4/2009 | Williams | |
| 2009/0209730 A1* | 8/2009 | Asada | C12N 9/1088 |
| | | | 536/23.5 |
| 2010/0255003 A1 | 10/2010 | Mevorach et al. | |
| 2014/0011978 A1 | 1/2014 | Hubbell et al. | |
| 2014/0377270 A1* | 12/2014 | Moore | C07K 16/2803 |
| | | | 435/69.6 |
| 2015/0266939 A1 | 9/2015 | Vogan et al. | |

FOREIGN PATENT DOCUMENTS

| | | | | |
|---|---|---|---|---|
| WO | WO-9526200 A1 * | 10/1995 | ......... | A01K 67/0271 |
| WO | 1999057150 | 11/1999 | | |
| WO | 2009132020 | 10/2009 | | |
| WO | 2009132020 A2 | 10/2009 | | |
| WO | 2011052638 | 5/2011 | | |
| WO | 2011052638 A1 | 5/2011 | | |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
Moritz et al., Blood 88: 855-862 (Year: 1996).*
Tur et al., International Journal of Cancer 129: 1277-1282 (Year: 2011).*
Yong et al., Scientific Reports 7 (42171): 1-12 (Year: 2017).*
Paul, Fundamental Immunology, (textbook), pp. 292-295 (Year: 1993).*
Green et al., Bioscience Horizons 7:1-10 (Year: 2014).*
Pollok et al., J Virology 72(6): 4882-4892 (Year: 1998).*
Silva et al., Immunology Letters 125: 129-136 (Year: 2009).*
Wu et al., J Virology 80(22): 11393-11397 (Year: 2006).*
Restriction Requirement issued Mar. 18, 2021 in U.S. Appl. No. 16/334,073.
Turtle et al., Artificial antigen presenting cells for use in adoptive immunotherapy, Cancer J. 2010; 16(4): 374-381 (2010).
International Search Report and Written Opinion in PCT/US2018/019181. Mailed Jun. 15, 2018.11 pages.
Albrecht, Huguette, Gerald L. DeNardo, and Sally J. DeNardo. "Monospecific bivalent scFv-SH: effects of linker length and location of an engineered cysteine on production, antigen binding activity and free SH accessibility." Journal of immunological methods 310.1-2 (2006): 100-116.
Argos, Patrick. "An investigation of oligopeptides linking domains in protein tertiary structures and possible candidates for general gene fusion." Journal of molecular biology 211.4 (1990): 943-958.
Bird, Robert E., et al. "Single-chain antigen-binding proteins." Science 242.4877 (1988): 423-426.

(Continued)

*Primary Examiner* — Phuong Huynh
(74) *Attorney, Agent, or Firm* — Meunier Carlin & Curfman LLC

(57) ABSTRACT

Disclosed are compositions and methods for gene transfer in immune effector cells, e.g. to create chimeric antigen receptors (CARs). In particular, polypeptides are disclosed that comprising an antigen-binding region and a heparin binding domain, wherein the antigen-binding region is capable of specifically binding to an immune cell antigen located on an immune effector cell, and wherein the heparin binding domain is capable of binding a viral vector.

11 Claims, 4 Drawing Sheets

Specification includes a Sequence Listing.

(56) References Cited

OTHER PUBLICATIONS

Fauriat, C., F. Mallet, and D. Olive. "Impaired activating receptor expression pattern in natural killer cells from patients with multiple myeloma." Leukemia 20.4 (2006): 732-733.
Feng, Jiannan, et al. "Design and assembly of anti-CD16 ScFv antibody with two different linker peptides." Journal of immunological methods 282.1-2 (2003): 33-43.
Godfrey, James, and Don M. Benson Jr. "The role of natural killer cells in immunity against multiple myeloma." Leukemia & lymphoma 53.9 (2012): 1666-1676.
Griffiths, Andrew D., and Alexander R. Duncan. "Strategies for selection of antibodies by phage display." Current opinion in biotechnology 9.1 (1998): 102-108.
Harlow et al. (Eds.), Antibodies: a Laboratory Manual; Cold Spring Harbor Laboratory; Cold Spring Harbor, N.Y., 1988, Chapter 6.
Holliger, Philipp, and Peter J. Hudson. "Engineered antibody fragments and the rise of single domains." Nature biotechnology 23.9 (2005): 1126.
Huston, James S., et al. "[3] Protein engineering of single-chain Fv analogs and fusion proteins." Methods in enzymology. vol. 203. Academic Press, 1991. 46-88.
International Preliminary Report on Patentability Application No. PCT/US2017/052152, dated Mar. 28, 2019.
International Search Report and Written Opinion issued for Application No. PCT/US2017/052152, dated Dec. 15, 2017.
International Preliminary Report on Patentability Application No. PCT/US2018/019181, dated Aug. 27, 2019.
International Search Report and Written Opinion issued for Application No. PCT/US2018/019181, dated Jun. 15, 2018.
Kumada, Yoichi, et al. "Polypeptide linkers suitable for the efficient production of dimeric scFv in *Escherichia coli*." Biochemical engineering journal 35.2 (2007): 158-165.
Morgan, Richard A., et al. "Case report of a serious adverse event following the administration of T cells transduced with a chimeric antigen receptor recognizing ERBB2." Molecular Therapy 18.4 (2010): 843-851.
Narni-Mancinelli, Emilie, Eric Vivier, and Yann M. Kerdiles. "The 'T-cell-ness' of NK cells: unexpected similarities between NK cells and T cells." International immunology 23.7 (2011): 427-431.
Porter, David L., et al. "Chimeric antigen receptor-modified T cells in chronic lymphoid leukemia." New England Journal of Medicine 365.8 (2011): 725-733.
Smallshaw, Joan E., et al. "Synthesis, cloning and expression of the single-chain Fv gene of the HPr-specific monoclonal antibody, Je142. Determination of binding constants with wild-type and mutant HPrs." Protein engineering 12.7 (1999): 623-630.
Takkinen, Kristiina, et al. "An active single-chain antibody containing a cellulase linker domain is secreted by *Escherichia coli*." Protein Engineering, Design and Selection 4.7 (1991): 837-841.
Turtle, Cameron J., and Stanley R. Riddell. "Artificial antigen presenting cells for use in adoptive immunotherapy". Cancer journal 16.4 (2010): 374-381.
Whitlow, Mare, et al. "An improved linker for single-chain Fv with reduced aggregation and enhanced proteolytic stability." Protein Engineering, Design and Selection 6.8 (1993): 989-995.
Office Action issued in U.S. Appl. No. 16/334,073 dated Oct. 29, 2021, 20 pages.
Hanspal et al., "The association of erythroblasts with macrophages promotes erythroid proliferation and maturation: a 30-kD heparin-binding protein is involved in this contact." Blood, vol. 84, No. 10, Nov. 15, 1994, pp. 3494-3504.
Lamers et al., "T cell receptor-engineered T cells to treat solid tumors: T cell processing toward optimal T cell fitness." Human gene therapy methods 25.6, Dec. 2014, pp. 345-357.
Baneyx et al., "Fibronectin extension and unfolding within cell matrix fibrils controlled by cytoskeletal tension." Proceedings of the National Academy of Sciences, vol. 99, No. 8, Apr. 16, 2002, pp. 5139-5143.
Butler et al., "Human cell-based artificial antigen-presenting cells for cancer immunotherapy." Immunological reviews 257(1), Jan. 2014, pp. 191-209.
Kim et al., "The ABCs of artificial antigen presentation." Nature biotechnology vol. 22, No. 4, Apr. 2004, pp. 403-410.
Stock, et al., "Optimizing manufacturing protocols of chimeric antigen receptor T cells for improved anticancer immunotherapy." International journal of molecular sciences vol. 20, No. 24, 2019, p. 6223.
Riella, Leonardo V., et al. "Role of the PD-1 pathway in the immune response." American Journal of Transplantation 12.10 (2012): 2575-2587.

\* cited by examiner

BISPECIFIC ANTIBODY FOR CANCER IMMUNOTHERAPY

CROSS-REFERENCE TO RELATED APPLICATIONS

This application claims benefit of U.S. Provisional Application No. 62/462,057, filed Feb. 22, 2017, incorporated herein by reference in its entirety.

BACKGROUND

Adoptive T cell immunotherapy offers a promising strategy for specifically targeting and eliminating cancerous cells. T cells can be engineered ex vivo to express chimeric antigen receptors specific for tumor antigens (CAR T cells). The expansion and function of adoptively transferred CAR T cells can be potentiated by the lymphodepletive and tumoricidal effects of standard of care chemotherapy and radiotherapy.

Production of CAR T cells currently involves isolation and activation of T cells from peripheral blood mononuclear cell (PBMC) with anti-CD3/anti-CD28 paramagnetic beads. The T cells are added to culture containers pre-treated with RetroNectin® and incubated with viral particles for gene transfer. The cells, beads and virus are incubated and the gene-modified cells are expanded. The beads and RetroNectin® are expensive and are limited in supply. Furthermore, the paramagnetic beads are also limited in their ability to be conjugated with more antibodies to activate and/or co-stimulate immune cells due to their small size.

SUMMARY

Disclosed is a less costly, renewable, modifiable, and efficacious alternative to coated beads and RetroNectin® for gene transfer. Disclosed are fusion polypeptides comprising 1) variable domains of antibodies that specifically bind an immune cell antigen and 2) a heparin binding domain (HBD). Antibodies binding immune cell antigens, such as CD3, CD28, or CD137, bind and activate expanding T cells ex vivo, while the HBD binds the viral vector, thereby bringing the T cells into close proximity with viral particles for effective gene transfer.

In some embodiments, the fusion polypeptide has the following formula:

$V_L I$-$V_H I$--HBD-Fc, $V_H I$-$V_L I$--HBD-Fc,

HBD--$V_L I$-$V_H I$-Fc,

HBD--$V_H$-$V_L I$-Fc,

Fc-$V_L I$-$V_H I$-HBD,

Fc-$V_H I$-$V_L I$-HBD,

Fc-HBD--$V_L I$-$V_H I$, or

Fc-HBD--$V_H I$-$V_L I$, wherein "$V_L I$" is a light chain variable domain specific for an immune cell antigen;
wherein "$V_H I$" is a heavy chain variable domain specific for the immune cell antigen;
wherein "HBD" is a heparin binding domain;
wherein "-" consists of a peptide linker or a peptide bond;
wherein "--" consists of a peptide linker or a peptide bond; and
wherein "Fc" consist of an optional Fc domain of an immunoglobulin.

The Fc ("fragment crystalline") portion of an antibody molecule includes the CH2 and CH3 domains of the heavy chain and a portion of the hinge region. It was originally defined by digestion of an IgG molecule with papain. Fc is responsible for two of the highly desirable properties of an IgG: recruitment of effector function and a long serum half-life. In some embodiments, the polypeptide sequence of an Fc domain is substantially similar to an Fc polypeptide sequence of: an IgG1 Fc region, an IgG2 Fc region, an IgG3 Fc region, an IgG4 Fc region, an IgM Fc region, an IgA Fc region, an IgD Fc region, or an IgE Fc region. In some embodiments, the Fc domain refers to the last two constant region immunoglobulin domains of IgA, IgD, and IgG, and the last three constant region immunoglobulin domains of IgE and IgM. In some embodiments, the disclosed fusion polypeptide can comprise one to four domains selected from the group consisting of CH1, CH2, CH3 and CH4 of IgG1, IgG2, IgG3 or IgG4, and may include a hinge region. The CH1, CH2, and/or CH3 domains may be derived from humans or other animals including cows, goats, swine, mice, rabbits, hamsters, rats and guinea pigs, and preferably humans, or synthetic, or a combination thereof. In addition, the Fc portion may be derived from IgG, IgA, IgD, IgE and IgM, or can be made by combinations thereof or hybrids thereof. Sequences for Fc domains are known in the art and publicly available.

The immune cell antigen can be a cell surface molecule that is expressed on human NK cells, T cells, monocytes, macrophages or granulocytes. For example, the cell surface molecule can be antigen CD2, CD3, CD16, CD64, CD89, CD137 (4-1BB), NKp30, NKp44, NKp46, NKp80 (KLR-F1), NKG2C or NKG2D.

In some embodiments, the anti-CD3 scFv comprises the amino acid sequence:

```
                                        (SEQ ID NO: 1)
MASPLTRFLSLNLLLLGESIILGSGEAQVQLQESGAELARPGASVKMSCK

ASGYTFTRYTMHWVKQRPGQGLEWIGYINPSRGYTNYNQKFKDKATLTTD

KSSSTAYMQLSSLTSEDSAVYYCARYYDDHYCLDYWGQGTTVTVSSGGGG

SGGGGSGGGGSDIQLTQSPAIMSASPGEKVTMTCSASSSVSYMNWYQQKS

GTSPKRWIYDTSKLASGVPAHFRGSGSGTSYSLTISGMEAEDAATYYCQQ

WSSNPFTFGSGTKLEIKR.
```

In some embodiments, the anti-CD28 scFv comprises the amino acid sequence:

```
                                        (SEQ ID NO: 2)
MASPLTRFLSLNLLLLGESIILGSGEAQVQLQQSGTELVKPASSVKISCK

ASGYTSTSNYMHWIRQQPGNGLEWIGRIYPGNGNTKYNQKFDGKATPTAD

KSSSTAYMQLSRLTFEDSAVYFCASAPLDYGGHIMDAWGQGTTVTVSSGG

GGSGGGGSGGGGSDIQLTQSPAFLSASLGETVSIECLGSEDIYGYLAWYQ

QKPGKSPQLLIYVANRLQDGVPSRFSGSGSGTQYSLKISGMQPEDEGDYY

CLQGSKFPLTFGSGTKLEIKR.
```

In some embodiments, the HBD comprises the amino acid sequence:

(SEQ ID NO: 3)
AIPAPTDLKFTQVTPTSLSAQWTPPNVQLTGYRVRVTPKEKTGPMKEINL

APDSSSVVVSGLMVATKYEVSVYALKDTLTSRPAQGVVTTLENVSPPRRA

RVTDATETTITISWRTKTETITGFQVDAVPANGQTPIQRTIKPDVRSYTI

TGLQPGTDYKIYLYTLNDNARSSPVVIDASTAIDAPSNLRFLATTPNSLL

VSWQPPRARITGYIIKYEKPGSPPREVVPRPRPGVTEATITGLEPGTEYT

IYVIALKNNQKSEPLIGRKKT.

Also disclosed is an isolated nucleic acid encoding the disclosed fusion polypeptide, as well as nucleic acid vectors containing this isolated nucleic acid operably linked to an expression control sequence. Also disclosed are cells transfected with these vectors and the use of these cells to produce the disclosed fusion polypeptides.

An antigen binding molecule can be formed from dimerization of heavy and light chains. In these embodiments, the $V_L I$ dimerizes with $V_H I$ to form an antigen binding site for an immune cell antigen (e.g., CD3).

Also disclosed is a fusion polypeptide comprising an antigen-binding region capable of recruiting the activity of a human immune effector cell by specifically binding to an immune cell antigen located on the human immune effector cell; and a heparin binding domain.

The antigen-binding region can be derived from natural antibodies, such as monoclonal antibodies. In some cases, the antibody is human. In some cases, the bispecific antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Currently, the most widely used technique for antibody human adaptation is known as "CDR grafting." The scientific basis of this technology is that the binding specificity of an antibody resides primarily within the three hypervariable loops known as the complementarity determining regions (CDRs) of its light and heavy chain variable regions (V-regions), whereas the more conserved framework regions (framework, FW; framework region, FR) provide structure support function. By grafting the CDRs to an appropriately selected FW, some or all of the antibody-binding activity can be transferred to the resulting recombinant antibody.

CDR grafting is the selection of a most appropriate human antibody acceptor for the graft. Various strategies have been developed to select human antibody acceptors with the highest similarities to the amino acid sequences of donor CDRs or donor FW, or to the donor structures. All these "best fit" strategies, while appearing very rational, are in fact based on one assumption, i.e., a resulting recombinant antibody that is most similar (in amino acid sequence or in structure) to the original antibody will best preserve the original antigen binding activity.

Not all amino acids in the CDRs are involved in antigen binding. Thus, it has been proposed that the grafting of only those residues that are critical in antigen-antibody interaction—the so-called specificity determining residues grafting (SDR-grafting)—will further increase the content of human antibody sequences in the resulting recombinant antibody.

The application of this strategy requires information on the antibody structure as well as antibody-antigen contact residues, which are quite often unavailable. Even when such information is available, there is no systematic method to reliably identify the SDRs, and SDR-grafting remains so far mostly at the basic research level.

Recently, a strategy called "human framework shuffling" has been developed. This technique works by ligating DNA fragments encoding CDRs to DNA fragments encoding human FR1, FR2, FR3, and FR4, thus generating a library of all combinations between donor CDRs and human FRs. Methods for making human-adapted antibodies based on molecular structures, modeling and sequences for human engineering of antibody molecules are disclosed in U.S. Pat. No. 8,748,356, which is incorporated by reference for these methods.

The effector cell recruited by the bispecific antibody is one capable of exerting a cytotoxic or an apoptotic effect on a target cell. In some embodiments, the human effector cell can in some embodiments be a member of the human lymphoid lineage or myeloid lineage. As an example, for lymphoid cells, the immune cell antigen can be selected from the group consisting of human CD3 antigen, human CD16 antigen, human NKG2D antigen, human CD2 antigen, human CD28 antigen, and human CD25 antigen. Similarly, for myeloid cells, the immune cell antigen can be human CD64 antigen or human CD89 antigen.

Also disclosed is a pharmaceutical composition comprising a molecule disclosed herein in a pharmaceutically acceptable carrier.

Also disclosed herein are methods for treating cancer in a subject comprising administering to the subject a therapeutically effective amount of a disclosed pharmaceutical composition.

Also disclosed is a kit comprising a bispecific antibody disclosed herein.

Also disclosed is an expression vector comprising an isolated nucleic acid encoding a bispecific antibody disclosed herein operably linked to an expression control sequence. Also disclosed is a cell comprising the disclosed expression vector. The cell can be a primary cell, transformed cell, cell line, or the like. In some cases, the cell is a mammalian cell line. In some cases, the cell is a non-mammalian cell line. For example, the cell can be a bacteria or insect cell line.

The details of one or more embodiments of the invention are set forth in the accompanying drawings and the description below. Other features, objects, and advantages of the invention will be apparent from the description and drawings, and from the claims.

Figure 1:
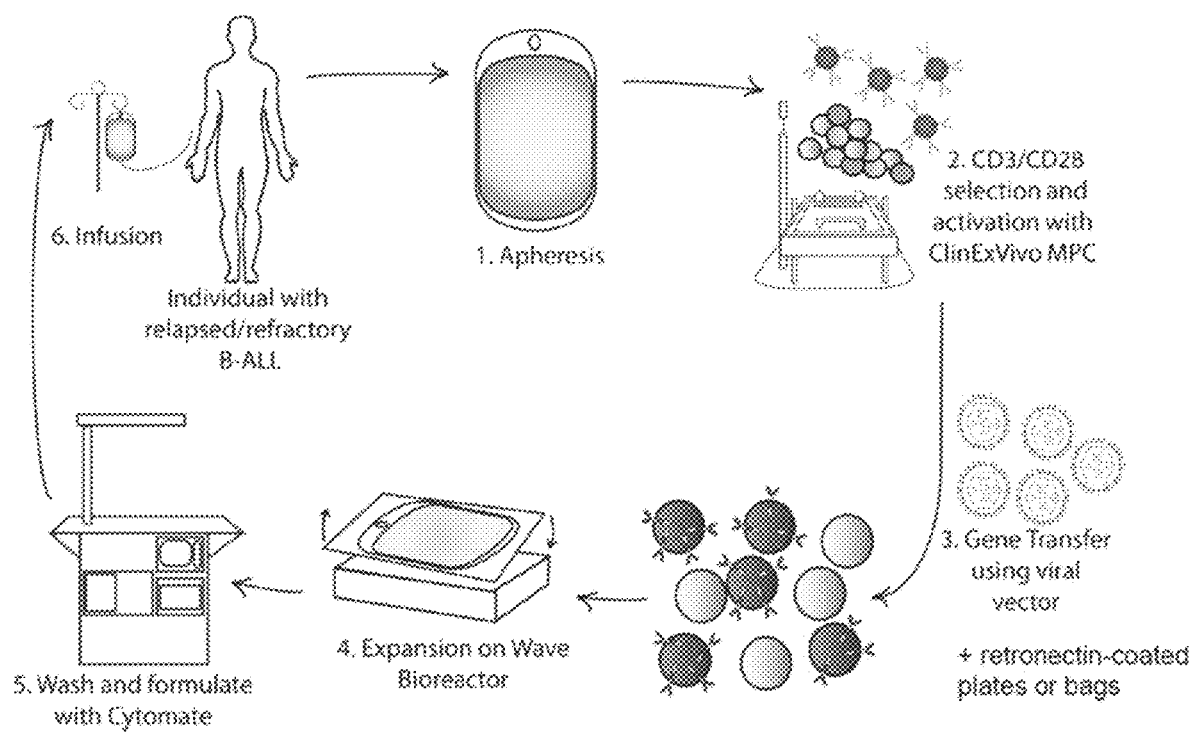
FIG. 1 illustrates the prior art method for CAR T cell production with beads and retronectin.
Figure 2:
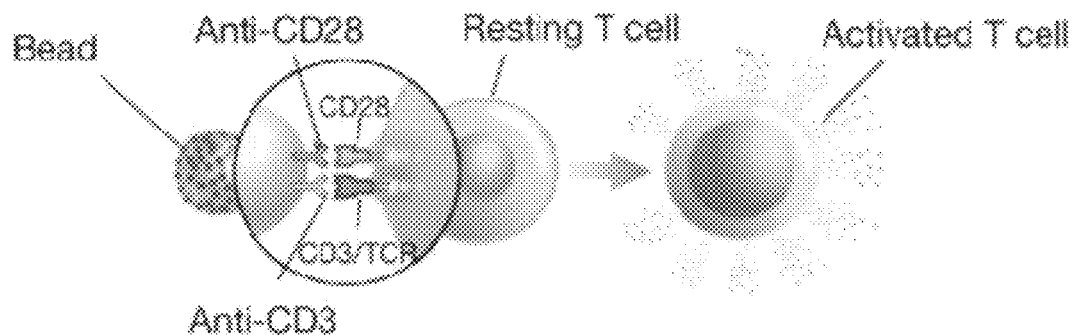
FIG. 2 illustrates critical reagents for prior art GMP CAR-T cell production.
Figure 2:
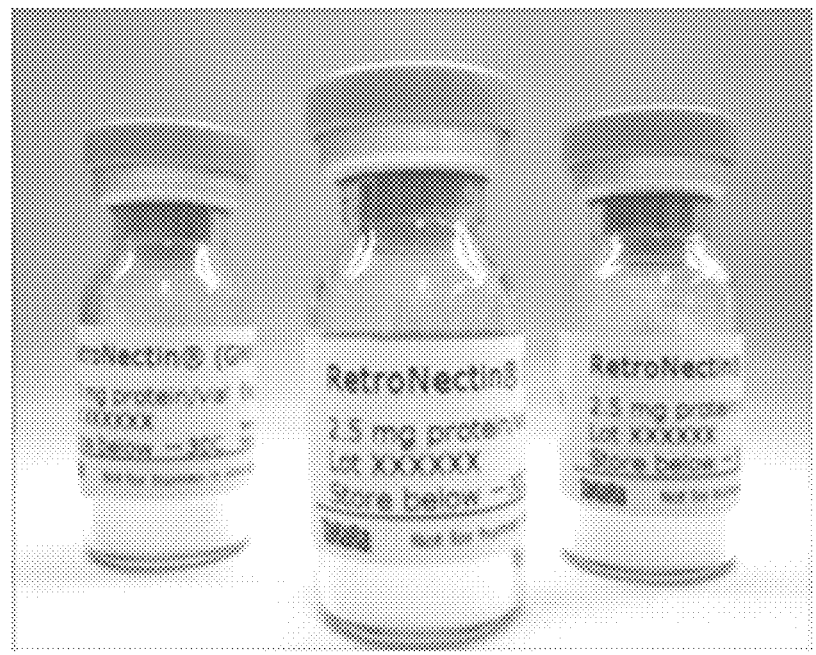
Figure 3:
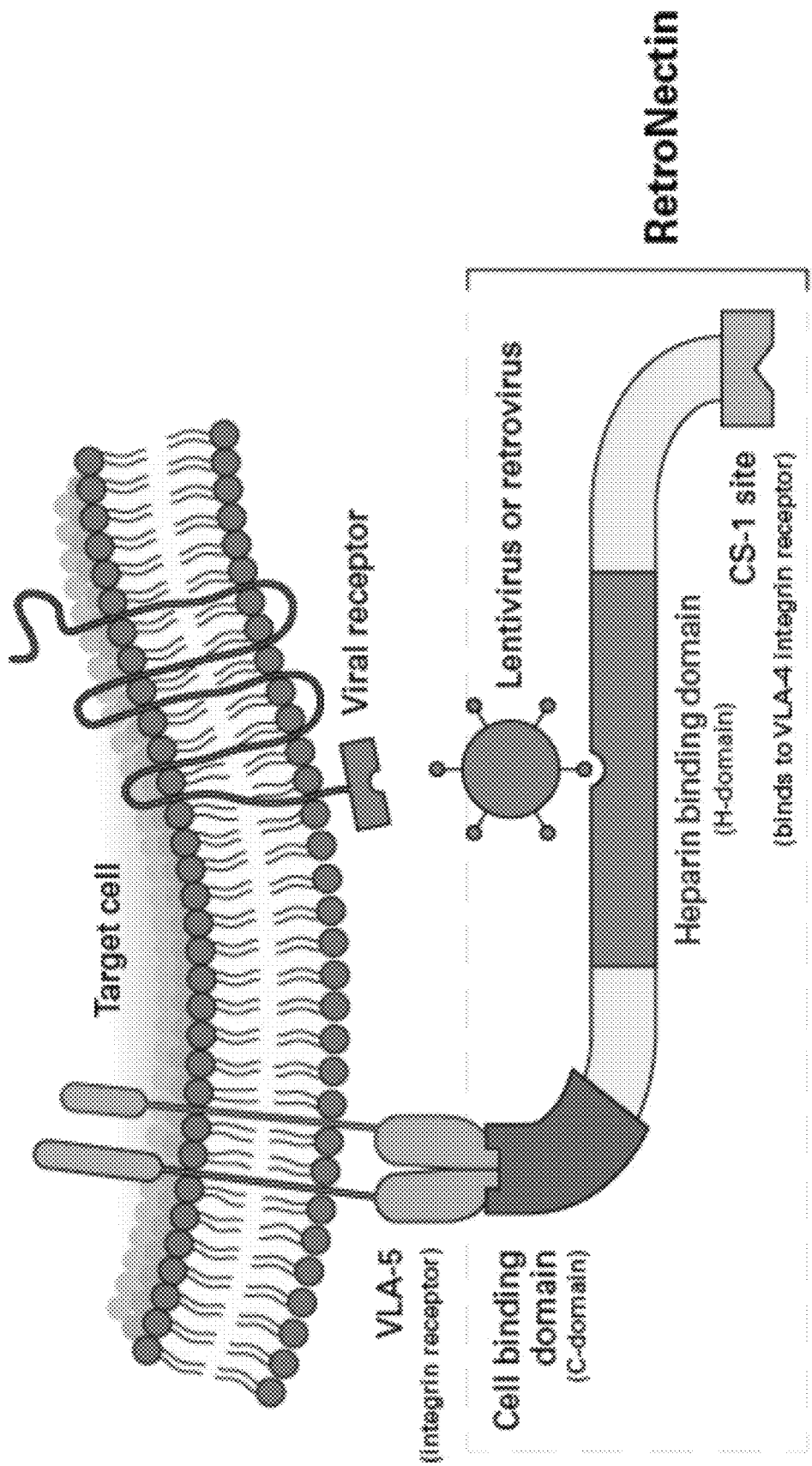
FIG. 3 illustrates how RetroNectin binds T cells and virus.
Figure 4:
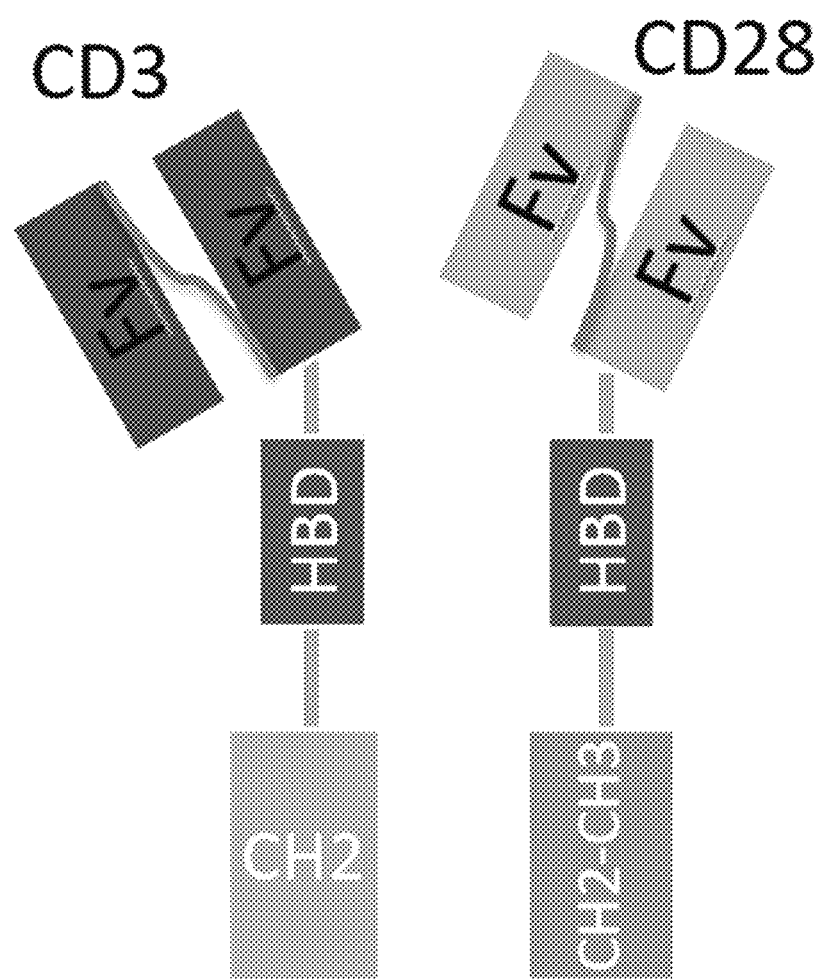
FIG. 4 illustrates an example synthetic antibody to engage CD3 or CD28 that contains a heparin binding domain.

DETAILED DESCRIPTION

Disclosed are fusion polypeptides comprising 1) variable domains of antibodies that specifically bind an immune cell antigen and 2) a heparin binding domain (HBD). The fusion polypeptides may comprise for example, at least one single chain antibody (scFv), at least one Fab fragment, at least one antibody, at least one Fv fragment, or any combination thereof. The scFv, Fab, or antibody encoded by the fusion polypeptide may be bivalent, trivalent, tetravalent, etc. Where a particular scFv is disclosed and said polypeptide are, it is understood that the multivalent antibodies can be multi-specific, e.g., bispecific, trispecific, tetraspecific, etc. The multivalent antibodies may be in any form, such as a diabody, triabody, tetrabody, etc.

Single chain antibodies may contain a heavy chain comprising one or more variable regions and/or a light chain comprising one or more variable regions. Single chain antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular $V_H$-$V_L$ pairings with formation of a 60 kDa non-covalent scFv dimer "diabody". The diabody format can also be used for generation of recombinant bi-specific antibodies, which are obtained by the noncovalent association of two single-chain fusion products, consisting of the $V_H$ domain from one antibody connected by a short linker to the $V_L$ domain of another antibody. Reducing the linker length still further below three residues can result in the formation of trimers ("triabody", about 90 kDa) or tetramers ("tetrabody", about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein.

Peptide linkers (-) suitable for production of scFv antibodies are described in Kumada Y, et al. Biochemical Engineering Journal. 2007 35(2):158-165; Albrecht H, et al J Immunol Methods. 2006 310(1-2):100-16; Feng J, et al. J Immunol Methods. 2003 282(1-2):33-43; Griffiths A D, et al. Curr Opin Biotechnol. 1998 9(1):102-8; Huston J S, et al. Methods Enzymol. 1991 203:46-88; Bird R E, et al. Science. 1988 242(4877):423-6; Takkinen K, et al. Protein Eng. 1991 4(7):837-41; Smallshaw J E, et al. Protein Eng. 1999 12(7): 623-30; Argos P. J Mol Biol. 1990 211(4):943-58; and Whitlow M, et al. Protein Eng. 1993 6(8):989-95, which are hereby incorporated by reference for the teachings of these linkers and methods of producing scFv antibodies against different targets using various linkers.

Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest. The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

The particular length of the peptide linker (--) used to join the scFv molecules to the heparin binding domain is important in determining half-life, immunogenicity, and activity of the overall construct. In some embodiments, the linker sequence (--) is 4, 5, 6, 7, 8, 9, 10, 11, 12, 13, 14, 15, 16, 17, 18, 19, 20, 21, 22, 23, 24, 25 or more amino acids in length.

In some embodiments, the linker sequence (--) comprises GGGGS (SEQ ID NO:4). In some cases, the linker comprises 2, 3, 4, 5, or more GGGGS sequences. The linker is preferably long enough to not interfere with proper folding and association of the $V_H$-$V_L$ chains but not so long as to cause added immunogenicity.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

In some embodiments, the bispecific antibody may be subjected to an alteration to render it less immunogenic when administered to a human. Such an alteration may comprise one or more of the techniques commonly known as chimerization, humanization, CDR-grafting, deimmunization and/or mutation of framework region amino acids to correspond to the closest human germline sequence (germlining) Bispecific antibodies which have been altered will therefore remain administrable for a longer period of time with reduced or no immune response-related side effects than corresponding bispecific antibodies which have not undergone any such alteration(s). One of ordinary skill in the art will understand how to determine whether, and to what degree an antibody must be altered in order to prevent it from eliciting an unwanted host immune response.

In some embodiments, the disclosed fusion polypeptide comprises a construct set forth in Table 1, 2, 3, or 4.

TABLE 1

| CD3-targeting constructs | | |
|---|---|---|
| CD3 scFv | HBD | CH1 |
| CD3 scFv | HBD | CH2 |
| CD3 scFv | HBD | CH3 |
| CD3 scFv | HBD | CH1—CH2 |
| CD3 scFv | HBD | CH1—CH3 |
| CD3 scFv | HBD | CH2—CH1 |
| CD3 scFv | HBD | CH2—CH3 |
| CD3 scFv | HBD | CH3—CH1 |
| CD3 scFv | HBD | CH3—CH2 |
| CD3 scFv | HBD | CH1—CH2—CH3 |
| CD3 scFv | HBD | CH1—CH3—CH2 |
| CD3 scFv | HBD | CH2—CH1—CH3 |
| CD3 scFv | HBD | CH2—CH3—CH1 |
| CD3 scFv | HBD | CH3—CH1—CH2 |
| CD3 scFv | HBD | CH3—CH2—CH1 |
| CH1 | HBD | CD3 scFv |
| CH2 | HBD | CD3 scFv |
| CH3 | HBD | CD3 scFv |
| CH1—CH2 | HBD | CD3 scFv |
| CH1—CH3 | HBD | CD3 scFv |
| CH2—CH1 | HBD | CD3 scFv |
| CH2—CH3 | HBD | CD3 scFv |
| CH3—CH1 | HBD | CD3 scFv |
| CH3—CH2 | HBD | CD3 scFv |
| CH1—CH2—CH3 | HBD | CD3 scFv |
| CH1—CH3—CH2 | HBD | CD3 scFv |
| CH2—CH1—CH3 | HBD | CD3 scFv |
| CH2—CH3—CH1 | HBD | CD3 scFv |
| CH3—CH1—CH2 | HBD | CD3 scFv |
| CH3—CH2—CH1 | HBD | CD3 scFv |
| HBD | CD3 scFv | CH1 |
| HBD | CD3 scFv | CH2 |
| HBD | CD3 scFv | CH3 |
| HBD | CD3 scFv | CH1—CH2 |
| HBD | CD3 scFv | CH1—CH3 |
| HBD | CD3 scFv | CH2—CH1 |
| HBD | CD3 scFv | CH2—CH3 |

TABLE 1-continued

| CD3-targeting constructs | | |
|---|---|---|
| HBD | CD3 scFv | CH3—CH1 |
| HBD | CD3 scFv | CH3—CH2 |
| HBD | CD3 scFv | CH1—CH2—CH3 |
| HBD | CD3 scFv | CH1—CH3—CH2 |
| HBD | CD3 scFv | CH2—CH1—CH3 |
| HBD | CD3 scFv | CH2—CH3—CH1 |
| HBD | CD3 scFv | CH3—CH1—CH2 |
| HBD | CD3 scFv | CH3—CH2—CH1 |

TABLE 2

| CD28-targeting constructs: | | |
|---|---|---|
| CD28 scFv | HBD | CH1 |
| CD28 scFv | HBD | CH2 |
| CD28 scFv | HBD | CH3 |
| CD28 scFv | HBD | CH1—CH2 |
| CD28 scFv | HBD | CH1—CH3 |
| CD28 scFv | HBD | CH2—CH1 |
| CD28 scFv | HBD | CH2—CH3 |
| CD28 scFv | HBD | CH3—CH1 |
| CD28 scFv | HBD | CH3—CH2 |
| CD28 scFv | HBD | CH1—CH2—CH3 |
| CD28 scFv | HBD | CH1—CH3—CH2 |
| CD28 scFv | HBD | CH2—CH1—CH3 |
| CD28 scFv | HBD | CH2—CH3—CH1 |
| CD28 scFv | HBD | CH3—CH1—CH2 |
| CD28 scFv | HBD | CH3—CH2—CH1 |
| CH1 | HBD | CD28 scFv |
| CH2 | HBD | CD28 scFv |
| CH3 | HBD | CD28 scFv |
| CH1—CH2 | HBD | CD28 scFv |
| CH1—CH3 | HBD | CD28 scFv |
| CH2—CH1 | HBD | CD28 scFv |
| CH2—CH3 | HBD | CD28 scFv |
| CH3—CH1 | HBD | CD28 scFv |
| CH3—CH2 | HBD | CD28 scFv |
| CH1—CH2—CH3 | HBD | CD28 scFv |
| CH1—CH3—CH2 | HBD | CD28 scFv |
| CH2—CH1—CH3 | HBD | CD28 scFv |
| CH2—CH3—CH1 | HBD | CD28 scFv |
| CH3—CH1—CH2 | HBD | CD28 scFv |
| CH3—CH2—CH1 | HBD | CD28 scFv |
| HBD | CD28 scFv | CH1 |
| HBD | CD28 scFv | CH2 |
| HBD | CD28 scFv | CH3 |
| HBD | CD28 scFv | CH1—CH2 |
| HBD | CD28 scFv | CH1—CH3 |
| HBD | CD28 scFv | CH2—CH1 |
| HBD | CD28 scFv | CH2—CH3 |
| HBD | CD28 scFv | CH3—CH1 |
| HBD | CD28 scFv | CH3—CH2 |
| HBD | CD28 scFv | CH1—CH2—CH3 |
| HBD | CD28 scFv | CH1—CH3—CH2 |
| HBD | CD28 scFv | CH2—CH1—CH3 |

TABLE 2-continued

| CD28-targeting constructs: | | |
|---|---|---|
| HBD | CD28 scFv | CH2—CH3—CH1 |
| HBD | CD28 scFv | CH3—CH1—CH2 |
| HBD | CD28 scFv | CH3—CH2—CH1 |

TABLE 3

| CD137/4-1BB-targeting constructs: | | |
|---|---|---|
| CD137 scFv | HBD | CH1 |
| CD137 scFv | HBD | CH2 |
| CD137 scFv | HBD | CH3 |
| CD137 scFv | HBD | CH1—CH2 |
| CD137 scFv | HBD | CH1—CH3 |
| CD137 scFv | HBD | CH2—CH1 |
| CD137 scFv | HBD | CH2—CH3 |
| CD137 scFv | HBD | CH3—CH1 |
| CD137 scFv | HBD | CH3—CH2 |
| CD137 scFv | HBD | CH1—CH2—CH3 |
| CD137 scFv | HBD | CH1—CH3—CH2 |
| CD137 scFv | HBD | CH2—CH1—CH3 |
| CD137 scFv | HBD | CH2—CH3—CH1 |
| CD137 scFv | HBD | CH3—CH1—CH2 |
| CD137 scFv | HBD | CH3—CH2—CH1 |
| CH1 | HBD | CD137 scFv |
| CH2 | HBD | CD137 scFv |
| CH3 | HBD | CD137 scFv |
| CH1—CH2 | HBD | CD137 scFv |
| CH1—CH3 | HBD | CD137 scFv |
| CH2—CH1 | HBD | CD137 scFv |
| CH2—CH3 | HBD | CD137 scFv |
| CH3—CH1 | HBD | CD137 scFv |
| CH3—CH2 | HBD | CD137 scFv |
| CH1—CH2—CH3 | HBD | CD137 scFv |
| CH1—CH3—CH2 | HBD | CD137 scFv |
| CH2—CH1—CH3 | HBD | CD137 scFv |
| CH2—CH3—CH1 | HBD | CD137 scFv |
| CH3—CH1—CH2 | HBD | CD137 scFv |
| CH3—CH2—CH1 | HBD | CD137 scFv |
| HBD | CD137 scFv | CH1 |
| HBD | CD137 scFv | CH2 |
| HBD | CD137 scFv | CH3 |
| HBD | CD137 scFv | CH1—CH2 |
| HBD | CD137 scFv | CH1—CH3 |
| HBD | CD137 scFv | CH2—CH1 |
| HBD | CD137 scFv | CH2—CH3 |
| HBD | CD137 scFv | CH3—CH1 |
| HBD | CD137 scFv | CH3—CH2 |
| HBD | CD137 scFv | CH1—CH2—CH3 |
| HBD | CD137 scFv | CH1—CH3—CH2 |
| HBD | CD137 scFv | CH2—CH1—CH3 |
| HBD | CD137 scFv | CH2—CH3—CH1 |
| HBD | CD137 scFv | CH3—CH1—CH2 |
| HBD | CD137 scFv | CH3—CH2—CH1 |

TABLE 4

| CD3- and CD28- and CD137/4-1BB-targeting constructs: | | | | |
|---|---|---|---|---|
| CD3 scFv | CD28 scFv | CD137 scFv | HBD | CH1 |
| CD3 scFv | CD28 scFv | CD137 scFv | HBD | CH2 |
| CD3 scFv | CD28 scFv | CD137 scFv | HBD | CH3 |
| CD3 scFv | CD28 scFv | CD137 scFv | HBD | CH1—CH2 |
| CD3 scFv | CD28 scFv | CD137 scFv | HBD | CH1—CH3 |
| CD3 scFv | CD28 scFv | CD137 scFv | HBD | CH2—CH1 |
| CD3 scFv | CD28 scFv | CD137 scFv | HBD | CH2—CH3 |
| CD3 scFv | CD28 scFv | CD137 scFv | HBD | CH3—CH1 |
| CD3 scFv | CD28 scFv | CD137 scFv | HBD | CH3—CH2 |
| CD3 scFv | CD28 scFv | CD137 scFv | HBD | CH1—CH2—CH3 |
| CD3 scFv | CD28 scFv | CD137 scFv | HBD | CH1—CH3—CH2 |
| CD3 scFv | CD28 scFv | CD137 scFv | HBD | CH2—CH1—CH3 |
| CD3 scFv | CD28 scFv | CD137 scFv | HBD | CH2—CH3—CH1 |
| CD3 scFv | CD28 scFv | CD137 scFv | HBD | CH3—CH1—CH2 |

TABLE 4-continued

| CD3- and CD28- and CD137/4-1BB-targeting constructs: | | | | |
|---|---|---|---|---|
| CD3 scFv | CD28 scFv | CD137 scFv | HBD | CH3—CH2—CH1 |
| CD3 scFv | CD137 scFv | CD28 scFv | HBD | CH1 |
| CD3 scFv | CD137 scFv | CD28 scFv | HBD | CH2 |
| CD3 scFv | CD137 scFv | CD28 scFv | HBD | CH3 |
| CD3 scFv | CD137 scFv | CD28 scFv | HBD | CH1—CH2 |
| CD3 scFv | CD137 scFv | CD28 scFv | HBD | CH1—CH3 |
| CD3 scFv | CD137 scFv | CD28 scFv | HBD | CH2—CH1 |
| CD3 scFv | CD137 scFv | CD28 scFv | HBD | CH2—CH3 |
| CD3 scFv | CD137 scFv | CD28 scFv | HBD | CH3—CH1 |
| CD3 scFv | CD137 scFv | CD28 scFv | HBD | CH3—CH2 |
| CD3 scFv | CD137 scFv | CD28 scFv | HBD | CH1—CH2—CH3 |
| CD3 scFv | CD137 scFv | CD28 scFv | HBD | CH1—CH3—CH2 |
| CD3 scFv | CD137 scFv | CD28 scFv | HBD | CH2—CH1—CH3 |
| CD3 scFv | CD137 scFv | CD28 scFv | HBD | CH2—CH3—CH1 |
| CD3 scFv | CD137 scFv | CD28 scFv | HBD | CH3—CH1—CH2 |
| CD3 scFv | CD137 scFv | CD28 scFv | HBD | CH3—CH2—CH1 |
| CD28 scFv | CD3 scFv | CD137 scFv | HBD | CH1 |
| CD28 scFv | CD3 scFv | CD137 scFv | HBD | CH2 |
| CD28 scFv | CD3 scFv | CD137 scFv | HBD | CH3 |
| CD28 scFv | CD3 scFv | CD137 scFv | HBD | CH1—CH2 |
| CD28 scFv | CD3 scFv | CD137 scFv | HBD | CH1—CH3 |
| CD28 scFv | CD3 scFv | CD137 scFv | HBD | CH2—CH1 |
| CD28 scFv | CD3 scFv | CD137 scFv | HBD | CH2—CH3 |
| CD28 scFv | CD3 scFv | CD137 scFv | HBD | CH3—CH1 |
| CD28 scFv | CD3 scFv | CD137 scFv | HBD | CH3—CH2 |
| CD28 scFv | CD3 scFv | CD137 scFv | HBD | CH1—CH2—CH3 |
| CD28 scFv | CD3 scFv | CD137 scFv | HBD | CH1—CH3—CH2 |
| CD28 scFv | CD3 scFv | CD137 scFv | HBD | CH2—CH1—CH3 |
| CD28 scFv | CD3 scFv | CD137 scFv | HBD | CH2—CH3—CH1 |
| CD28 scFv | CD3 scFv | CD137 scFv | HBD | CH3—CH1—CH2 |
| CD28 scFv | CD3 scFv | CD137 scFv | HBD | CH3—CH2—CH1 |
| CD28 scFv | CD137 scFv | CD3 scFv | HBD | CH1 |
| CD28 scFv | CD137 scFv | CD3 scFv | HBD | CH2 |
| CD28 scFv | CD137 scFv | CD3 scFv | HBD | CH3 |
| CD28 scFv | CD137 scFv | CD3 scFv | HBD | CH1—CH2 |
| CD28 scFv | CD137 scFv | CD3 scFv | HBD | CH1—CH3 |
| CD28 scFv | CD137 scFv | CD3 scFv | HBD | CH2—CH1 |
| CD28 scFv | CD137 scFv | CD3 scFv | HBD | CH2—CH3 |
| CD28 scFv | CD137 scFv | CD3 scFv | HBD | CH3—CH1 |
| CD28 scFv | CD137 scFv | CD3 scFv | HBD | CH3—CH2 |
| CD28 scFv | CD137 scFv | CD3 scFv | HBD | CH1—CH2—CH3 |
| CD28 scFv | CD137 scFv | CD3 scFv | HBD | CH1—CH3—CH2 |
| CD28 scFv | CD137 scFv | CD3 scFv | HBD | CH2—CH1—CH3 |
| CD28 scFv | CD137 scFv | CD3 scFv | HBD | CH2—CH3—CH1 |
| CD28 scFv | CD137 scFv | CD3 scFv | HBD | CH3—CH1—CH2 |
| CD28 scFv | CD137 scFv | CD3 scFv | HBD | CH3—CH2—CH1 |
| CD137 scFv | CD3 scFv | CD28 scFv | HBD | CH1 |
| CD137 scFv | CD3 scFv | CD28 scFv | HBD | CH2 |
| CD137 scFv | CD3 scFv | CD28 scFv | HBD | CH3 |
| CD137 scFv | CD3 scFv | CD28 scFv | HBD | CH1—CH2 |
| CD137 scFv | CD3 scFv | CD28 scFv | HBD | CH1—CH3 |
| CD137 scFv | CD3 scFv | CD28 scFv | HBD | CH2—CH1 |
| CD137 scFv | CD3 scFv | CD28 scFv | HBD | CH2—CH3 |
| CD137 scFv | CD3 scFv | CD28 scFv | HBD | CH3—CH1 |
| CD137 scFv | CD3 scFv | CD28 scFv | HBD | CH3—CH2 |
| CD137 scFv | CD3 scFv | CD28 scFv | HBD | CH1—CH2—CH3 |
| CD137 scFv | CD3 scFv | CD28 scFv | HBD | CH1—CH3—CH2 |
| CD137 scFv | CD3 scFv | CD28 scFv | HBD | CH2—CH1—CH3 |
| CD137 scFv | CD3 scFv | CD28 scFv | HBD | CH2—CH3—CH1 |
| CD137 scFv | CD3 scFv | CD28 scFv | HBD | CH3—CH1—CH2 |
| CD137 scFv | CD3 scFv | CD28 scFv | HBD | CH3—CH2—CH1 |
| CD137 scFv | CD28 scFv | CD3 scFv | HBD | CH1 |
| CD137 scFv | CD28 scFv | CD3 scFv | HBD | CH2 |
| CD137 scFv | CD28 scFv | CD3 scFv | HBD | CH3 |
| CD137 scFv | CD28 scFv | CD3 scFv | HBD | CH1—CH2 |
| CD137 scFv | CD28 scFv | CD3 scFv | HBD | CH1—CH3 |
| CD137 scFv | CD28 scFv | CD3 scFv | HBD | CH2—CH1 |
| CD137 scFv | CD28 scFv | CD3 scFv | HBD | CH2—CH3 |
| CD137 scFv | CD28 scFv | CD3 scFv | HBD | CH3—CH1 |
| CD137 scFv | CD28 scFv | CD3 scFv | HBD | CH3—CH2 |
| CD137 scFv | CD28 scFv | CD3 scFv | HBD | CH1—CH2—CH3 |
| CD137 scFv | CD28 scFv | CD3 scFv | HBD | CH1—CH3—CH2 |
| CD137 scFv | CD28 scFv | CD3 scFv | HBD | CH2—CH1—CH3 |
| CD137 scFv | CD28 scFv | CD3 scFv | HBD | CH2—CH3—CH1 |
| CD137 scFv | CD28 scFv | CD3 scFv | HBD | CH3—CH1—CH2 |
| CD137 scFv | CD28 scFv | CD3 scFv | HBD | CH3—CH2—CH1 |
| CH1 | HBD | CD3 scFv | CD28 scFv | CD137 scFv |
| CH2 | HBD | CD3 scFv | CD28 scFv | CD137 scFv |

TABLE 4-continued

| CD3- and CD28- and CD137/4-1BB-targeting constructs: | | | | |
|---|---|---|---|---|
| CH3 | HBD | CD3 scFv | CD28 scFv | CD137 scFv |
| CH1—CH2 | HBD | CD3 scFv | CD28 scFv | CD137 scFv |
| CH1—CH3 | HBD | CD3 scFv | CD28 scFv | CD137 scFv |
| CH2—CH1 | HBD | CD3 scFv | CD28 scFv | CD137 scFv |
| CH2—CH3 | HBD | CD3 scFv | CD28 scFv | CD137 scFv |
| CH3—CH1 | HBD | CD3 scFv | CD28 scFv | CD137 scFv |
| CH3—CH2 | HBD | CD3 scFv | CD28 scFv | CD137 scFv |
| CH1—CH2—CH3 | HBD | CD3 scFv | CD28 scFv | CD137 scFv |
| CH1—CH3—CH2 | HBD | CD3 scFv | CD28 scFv | CD137 scFv |
| CH2—CH1—CH3 | HBD | CD3 scFv | CD28 scFv | CD137 scFv |
| CH2—CH3—CH1 | HBD | CD3 scFv | CD28 scFv | CD137 scFv |
| CH3—CH1—CH2 | HBD | CD3 scFv | CD28 scFv | CD137 scFv |
| CH3—CH2—CH1 | HBD | CD3 scFv | CD28 scFv | CD137 scFv |
| CH1 | HBD | CD3 scFv | CD137 scFv | CD28 scFv |
| CH2 | HBD | CD3 scFv | CD137 scFv | CD28 scFv |
| CH3 | HBD | CD3 scFv | CD137 scFv | CD28 scFv |
| CH1—CH2 | HBD | CD3 scFv | CD137 scFv | CD28 scFv |
| CH1—CH3 | HBD | CD3 scFv | CD137 scFv | CD28 scFv |
| CH2—CH1 | HBD | CD3 scFv | CD137 scFv | CD28 scFv |
| CH2—CH3 | HBD | CD3 scFv | CD137 scFv | CD28 scFv |
| CH3—CH1 | HBD | CD3 scFv | CD137 scFv | CD28 scFv |
| CH3—CH2 | HBD | CD3 scFv | CD137 scFv | CD28 scFv |
| CH1—CH2—CH3 | HBD | CD3 scFv | CD137 scFv | CD28 scFv |
| CH1—CH3—CH2 | HBD | CD3 scFv | CD137 scFv | CD28 scFv |
| CH2—CH1—CH3 | HBD | CD3 scFv | CD137 scFv | CD28 scFv |
| CH2—CH3—CH1 | HBD | CD3 scFv | CD137 scFv | CD28 scFv |
| CH3—CH1—CH2 | HBD | CD3 scFv | CD137 scFv | CD28 scFv |
| CH3—CH2—CH1 | HBD | CD3 scFv | CD137 scFv | CD28 scFv |
| CH1 | HBD | CD28 scFv | CD3 scFv | CD137 scFv |
| CH2 | HBD | CD28 scFv | CD3 scFv | CD137 scFv |
| CH3 | HBD | CD28 scFv | CD3 scFv | CD137 scFv |
| CH1—CH2 | HBD | CD28 scFv | CD3 scFv | CD137 scFv |
| CH1—CH3 | HBD | CD28 scFv | CD3 scFv | CD137 scFv |
| CH2—CH1 | HBD | CD28 scFv | CD3 scFv | CD137 scFv |
| CH2—CH3 | HBD | CD28 scFv | CD3 scFv | CD137 scFv |
| CH3—CH1 | HBD | CD28 scFv | CD3 scFv | CD137 scFv |
| CH3—CH2 | HBD | CD28 scFv | CD3 scFv | CD137 scFv |
| CH1—CH2—CH3 | HBD | CD28 scFv | CD3 scFv | CD137 scFv |
| CH1—CH3—CH2 | HBD | CD28 scFv | CD3 scFv | CD137 scFv |
| CH2—CH1—CH3 | HBD | CD28 scFv | CD3 scFv | CD137 scFv |
| CH2—CH3—CH1 | HBD | CD28 scFv | CD3 scFv | CD137 scFv |
| CH3—CH1—CH2 | HBD | CD28 scFv | CD3 scFv | CD137 scFv |
| CH3—CH2—CH1 | HBD | CD28 scFv | CD3 scFv | CD137 scFv |
| CH1 | HBD | CD28 scFv | CD137 scFv | CD3 scFv |
| CH2 | HBD | CD28 scFv | CD137 scFv | CD3 scFv |
| CH3 | HBD | CD28 scFv | CD137 scFv | CD3 scFv |
| CH1—CH2 | HBD | CD28 scFv | CD137 scFv | CD3 scFv |
| CH1—CH3 | HBD | CD28 scFv | CD137 scFv | CD3 scFv |
| CH2—CH1 | HBD | CD28 scFv | CD137 scFv | CD3 scFv |
| CH2—CH3 | HBD | CD28 scFv | CD137 scFv | CD3 scFv |
| CH3—CH1 | HBD | CD28 scFv | CD137 scFv | CD3 scFv |
| CH3—CH2 | HBD | CD28 scFv | CD137 scFv | CD3 scFv |
| CH1—CH2—CH3 | HBD | CD28 scFv | CD137 scFv | CD3 scFv |
| CH1—CH3—CH2 | HBD | CD28 scFv | CD137 scFv | CD3 scFv |
| CH2—CH1—CH3 | HBD | CD28 scFv | CD137 scFv | CD3 scFv |
| CH2—CH3—CH1 | HBD | CD28 scFv | CD137 scFv | CD3 scFv |
| CH3—CH1—CH2 | HBD | CD28 scFv | CD137 scFv | CD3 scFv |
| CH3—CH2—CH1 | HBD | CD28 scFv | CD137 scFv | CD3 scFv |
| CH1 | HBD | CD137 scFv | CD3 scFv | CD28 scFv |
| CH2 | HBD | CD137 scFv | CD3 scFv | CD28 scFv |
| CH3 | HBD | CD137 scFv | CD3 scFv | CD28 scFv |
| CH1—CH2 | HBD | CD137 scFv | CD3 scFv | CD28 scFv |
| CH1—CH3 | HBD | CD137 scFv | CD3 scFv | CD28 scFv |
| CH2—CH1 | HBD | CD137 scFv | CD3 scFv | CD28 scFv |
| CH2—CH3 | HBD | CD137 scFv | CD3 scFv | CD28 scFv |
| CH3—CH1 | HBD | CD137 scFv | CD3 scFv | CD28 scFv |
| CH3—CH2 | HBD | CD137 scFv | CD3 scFv | CD28 scFv |
| CH1—CH2—CH3 | HBD | CD137 scFv | CD3 scFv | CD28 scFv |
| CH1—CH3—CH2 | HBD | CD137 scFv | CD3 scFv | CD28 scFv |
| CH2—CH1—CH3 | HBD | CD137 scFv | CD3 scFv | CD28 scFv |
| CH2—CH3—CH1 | HBD | CD137 scFv | CD3 scFv | CD28 scFv |
| CH3—CH1—CH2 | HBD | CD137 scFv | CD3 scFv | CD28 scFv |
| CH3—CH2—CH1 | HBD | CD137 scFv | CD3 scFv | CD28 scFv |
| CH1 | HBD | CD137 scFv | CD28 scFv | CD3 scFv |
| CH2 | HBD | CD137 scFv | CD28 scFv | CD3 scFv |
| CH3 | HBD | CD137 scFv | CD28 scFv | CD3 scFv |
| CH1—CH2 | HBD | CD137 scFv | CD28 scFv | CD3 scFv |
| CH1—CH3 | HBD | CD137 scFv | CD28 scFv | CD3 scFv |

TABLE 4-continued

| CD3- and CD28- and CD137/4-1BB-targeting constructs: | | | | |
|---|---|---|---|---|
| CH2—CH1 | HBD | CD137 scFv | CD28 scFv | CD3 scFv |
| CH2—CH3 | HBD | CD137 scFv | CD28 scFv | CD3 scFv |
| CH3—CH1 | HBD | CD137 scFv | CD28 scFv | CD3 scFv |
| CH3—CH2 | HBD | CD137 scFv | CD28 scFv | CD3 scFv |
| CH1—CH2—CH3 | HBD | CD137 scFv | CD28 scFv | CD3 scFv |
| CH1—CH3—CH2 | HBD | CD137 scFv | CD28 scFv | CD3 scFv |
| CH2—CH1—CH3 | HBD | CD137 scFv | CD28 scFv | CD3 scFv |
| CH2—CH3—CH1 | HBD | CD137 scFv | CD28 scFv | CD3 scFv |
| CH3—CH1—CH2 | HBD | CD137 scFv | CD28 scFv | CD3 scFv |
| CH3—CH2—CH1 | HBD | CD137 scFv | CD28 scFv | CD3 scFv |
| HBD | CD3 scFv | CD28 scFv | CD137 scFv | CH1 |
| HBD | CD3 scFv | CD28 scFv | CD137 scFv | CH2 |
| HBD | CD3 scFv | CD28 scFv | CD137 scFv | CH3 |
| HBD | CD3 scFv | CD28 scFv | CD137 scFv | CH1—CH2 |
| HBD | CD3 scFv | CD28 scFv | CD137 scFv | CH1—CH3 |
| HBD | CD3 scFv | CD28 scFv | CD137 scFv | CH2—CH1 |
| HBD | CD3 scFv | CD28 scFv | CD137 scFv | CH2—CH3 |
| HBD | CD3 scFv | CD28 scFv | CD137 scFv | CH3—CH1 |
| HBD | CD3 scFv | CD28 scFv | CD137 scFv | CH3—CH2 |
| HBD | CD3 scFv | CD28 scFv | CD137 scFv | CH1—CH2—CH3 |
| HBD | CD3 scFv | CD28 scFv | CD137 scFv | CH1—CH3—CH2 |
| HBD | CD3 scFv | CD28 scFv | CD137 scFv | CH2—CH1—CH3 |
| HBD | CD3 scFv | CD28 scFv | CD137 scFv | CH2—CH3—CH1 |
| HBD | CD3 scFv | CD28 scFv | CD137 scFv | CH3—CH1—CH2 |
| HBD | CD3 scFv | CD28 scFv | CD137 scFv | CH3—CH2—CH1 |
| HBD | CD3 scFv | CD137 scFv | CD28 scFv | CH1 |
| HBD | CD3 scFv | CD137 scFv | CD28 scFv | CH2 |
| HBD | CD3 scFv | CD137 scFv | CD28 scFv | CH3 |
| HBD | CD3 scFv | CD137 scFv | CD28 scFv | CH1—CH2 |
| HBD | CD3 scFv | CD137 scFv | CD28 scFv | CH1—CH3 |
| HBD | CD3 scFv | CD137 scFv | CD28 scFv | CH2—CH1 |
| HBD | CD3 scFv | CD137 scFv | CD28 scFv | CH2—CH3 |
| HBD | CD3 scFv | CD137 scFv | CD28 scFv | CH3—CH1 |
| HBD | CD3 scFv | CD137 scFv | CD28 scFv | CH3—CH2 |
| HBD | CD3 scFv | CD137 scFv | CD28 scFv | CH1—CH2—CH3 |
| HBD | CD3 scFv | CD137 scFv | CD28 scFv | CH1—CH3—CH2 |
| HBD | CD3 scFv | CD137 scFv | CD28 scFv | CH2—CH1—CH3 |
| HBD | CD3 scFv | CD137 scFv | CD28 scFv | CH2—CH3—CH1 |
| HBD | CD3 scFv | CD137 scFv | CD28 scFv | CH3—CH1—CH2 |
| HBD | CD3 scFv | CD137 scFv | CD28 scFv | CH3—CH2—CH1 |
| HBD | CD28 scFv | CD3 scFv | CD137 scFv | CH1 |
| HBD | CD28 scFv | CD3 scFv | CD137 scFv | CH2 |
| HBD | CD28 scFv | CD3 scFv | CD137 scFv | CH3 |
| HBD | CD28 scFv | CD3 scFv | CD137 scFv | CH1—CH2 |
| HBD | CD28 scFv | CD3 scFv | CD137 scFv | CH1—CH3 |
| HBD | CD28 scFv | CD3 scFv | CD137 scFv | CH2—CH1 |
| HBD | CD28 scFv | CD3 scFv | CD137 scFv | CH2—CH3 |
| HBD | CD28 scFv | CD3 scFv | CD137 scFv | CH3—CH1 |
| HBD | CD28 scFv | CD3 scFv | CD137 scFv | CH3—CH2 |
| HBD | CD28 scFv | CD3 scFv | CD137 scFv | CH1—CH2—CH3 |
| HBD | CD28 scFv | CD3 scFv | CD137 scFv | CH1—CH3—CH2 |
| HBD | CD28 scFv | CD3 scFv | CD137 scFv | CH2—CH1—CH3 |
| HBD | CD28 scFv | CD3 scFv | CD137 scFv | CH2—CH3—CH1 |
| HBD | CD28 scFv | CD3 scFv | CD137 scFv | CH3—CH1—CH2 |
| HBD | CD28 scFv | CD3 scFv | CD137 scFv | CH3—CH2—CH1 |
| HBD | CD28 scFv | CD137 scFv | CD3 scFv | CH1 |
| HBD | CD28 scFv | CD137 scFv | CD3 scFv | CH2 |
| HBD | CD28 scFv | CD137 scFv | CD3 scFv | CH3 |
| HBD | CD28 scFv | CD137 scFv | CD3 scFv | CH1—CH2 |
| HBD | CD28 scFv | CD137 scFv | CD3 scFv | CH1—CH3 |
| HBD | CD28 scFv | CD137 scFv | CD3 scFv | CH2—CH1 |
| HBD | CD28 scFv | CD137 scFv | CD3 scFv | CH2—CH3 |
| HBD | CD28 scFv | CD137 scFv | CD3 scFv | CH3—CH1 |
| HBD | CD28 scFv | CD137 scFv | CD3 scFv | CH3—CH2 |
| HBD | CD28 scFv | CD137 scFv | CD3 scFv | CH1—CH2—CH3 |
| HBD | CD28 scFv | CD137 scFv | CD3 scFv | CH1—CH3—CH2 |
| HBD | CD28 scFv | CD137 scFv | CD3 scFv | CH2—CH1—CH3 |
| HBD | CD28 scFv | CD137 scFv | CD3 scFv | CH2—CH3—CH1 |
| HBD | CD28 scFv | CD137 scFv | CD3 scFv | CH3—CH1—CH2 |
| HBD | CD28 scFv | CD137 scFv | CD3 scFv | CH3—CH2—CH1 |
| HBD | CD137 scFv | CD3 scFv | CD28 scFv | CH1 |
| HBD | CD137 scFv | CD3 scFv | CD28 scFv | CH2 |
| HBD | CD137 scFv | CD3 scFv | CD28 scFv | CH3 |
| HBD | CD137 scFv | CD3 scFv | CD28 scFv | CH1—CH2 |
| HBD | CD137 scFv | CD3 scFv | CD28 scFv | CH1—CH3 |
| HBD | CD137 scFv | CD3 scFv | CD28 scFv | CH2—CH1 |
| HBD | CD137 scFv | CD3 scFv | CD28 scFv | CH2—CH3 |
| HBD | CD137 scFv | CD3 scFv | CD28 scFv | CH3—CH1 |

TABLE 4-continued

| CD3- and CD28- and CD137/4-1BB-targeting constructs: | | | | |
|---|---|---|---|---|
| HBD | CD137 scFv | CD3 scFv | CD28 scFv | CH3—CH2 |
| HBD | CD137 scFv | CD3 scFv | CD28 scFv | CH1—CH2—CH3 |
| HBD | CD137 scFv | CD3 scFv | CD28 scFv | CH1—CH3—CH2 |
| HBD | CD137 scFv | CD3 scFv | CD28 scFv | CH2—CH1—CH3 |
| HBD | CD137 scFv | CD3 scFv | CD28 scFv | CH2—CH3—CH1 |
| HBD | CD137 scFv | CD3 scFv | CD28 scFv | CH3—CH1—CH2 |
| HBD | CD137 scFv | CD3 scFv | CD28 scFv | CH3—CH2—CH1 |
| HBD | CD137 scFv | CD28 scFv | CD3 scFv | CH1 |
| HBD | CD137 scFv | CD28 scFv | CD3 scFv | CH2 |
| HBD | CD137 scFv | CD28 scFv | CD3 scFv | CH3 |
| HBD | CD137 scFv | CD28 scFv | CD3 scFv | CH1—CH2 |
| HBD | CD137 scFv | CD28 scFv | CD3 scFv | CH1—CH3 |
| HBD | CD137 scFv | CD28 scFv | CD3 scFv | CH2—CH1 |
| HBD | CD137 scFv | CD28 scFv | CD3 scFv | CH2—CH3 |
| HBD | CD137 scFv | CD28 scFv | CD3 scFv | CH3—CH1 |
| HBD | CD137 scFv | CD28 scFv | CD3 scFv | CH3—CH2 |
| HBD | CD137 scFv | CD28 scFv | CD3 scFv | CH1—CH2—CH3 |
| HBD | CD137 scFv | CD28 scFv | CD3 scFv | CH1—CH3—CH2 |
| HBD | CD137 scFv | CD28 scFv | CD3 scFv | CH2—CH1—CH3 |
| HBD | CD137 scFv | CD28 scFv | CD3 scFv | CH2—CH3—CH1 |
| HBD | CD137 scFv | CD28 scFv | CD3 scFv | CH3—CH1—CH2 |
| HBD | CD137 scFv | CD28 scFv | CD3 scFv | CH3—CH2—CH1 |

Also disclosed is a method for gene transfer of an immune effector cell with a viral particle that involves co-culturing the immune effector cells with the viral particle and a fusion polypeptide disclosed herein. The disclosed antibodies can also be used in automated systems that are being developed for CAR T cell production, such as the MACs Prodigy.

Definitions

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "bispecific antibody" refers to an antibody having two different antigen-binding regions defined by different antibody sequences. This can be understood as different target binding but includes as well binding to different epitopes in one target.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "protein" (if single-chain), "polypeptide" and "peptide" are used interchangeably herein when referring to a gene product, e.g., as may be encoded by a coding sequence. When referring to "polypeptide" herein, a person of skill in the art will recognize that a protein can be used instead, unless the context clearly indicates otherwise. A "protein" may also refer to an association of one or more polypeptides. By "gene product" is meant a molecule that is produced as a result of transcription of a gene. Gene products include RNA molecules transcribed from a gene, as well as proteins translated from such transcripts.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e g immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

It is understood and herein contemplated that the fusion polypeptides disclosed herein are particularly useful in the treatment of cancer. Accordingly, disclosed herein are methods for treating cancer in a subject that involves administering to the subject a therapeutically effective amount of a disclosed pharmaceutical composition. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed fusion polypeptides can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed fusion polypeptides can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed fusion polypeptides can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

It is further contemplated herein that the disclosed fusion polypeptides can be used in combination with any known cancer therapeutic for the treatment of a cancer including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil--Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNIS ONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil--Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil--Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil--Topical), Fluorouracil Injection, Fluorouracil--Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perj eta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil--Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Protocol for scFVHBD Transduction

1. Add 100 µl of PBS diluted anti-CD3 and or anti-CD28 scFv+HBD proteins to each well of round-bottom 6-well assay plate: 1 µ/ml (final concentration)
2. Tightly cover the plate with Parafilm and incubate at 37° C. for 2 hr and keep at 4 overnight
3. Isolate T cells and culture on scFv+HBD-coated plates overnight at 37° C.
4. Spinoculation #1 (Day 2)
5. Harvest purified T-cells and spin cells at 700 g for 5 min
6. Dispense 1 mL of cells (2 to 3 millon T cells) onto each well of a 6-well plate that has been pre-coated with scFv+HBD-coated
7. Add 1 mL of virus into each well
8. Spin plates at 2000 g for 1 hr @ RT
9. Incubation
10. Transduction and Spinoculation #2 (Day 3)
11. Remove 850 µL of cultured media from each well
12. Add 1 mL of virus to each well
13. Spin plates at 2000 g for 1 hr @ RT
14. Incubation
15. Add c-RPMI media (Day 4)
16. Day 5 cells are ready for use Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A fusion polypeptide comprising an antigen-binding region and a heparin binding domain comprising the amino acid sequence SEQ ID NO:3, wherein the antigen-binding region is capable of specifically binding to an immune cell antigen located on an immune effector cell, and wherein the heparin binding domain is capable of binding a viral vector, and further wherein the immune cell antigen binding region comprises the amino acid sequence SEQ ID NO:1 or SEQ ID NO:2.

2. The polypeptide of claim 1, wherein the immune effector cell is a member of the human lymphoid lineage.

3. The polypeptide of claim 1, wherein the immune effector cell is capable of exerting a cytotoxic or an apoptotic effect on a target cell.

4. A fusion polypeptide comprising the following formula:

$V_LI$-$V_HI$--HBD-Fc, $V_HI$-$V_LI$--HBD-Fc,

HBD--$V_LI$-$V_HI$-Fc,

HBD--$V_H$-$V_LI$-Fc,

Fc-$V_LI$-$V_HI$-HBD,

Fc-$V_HI$-$V_LI$-HBD,

Fc-HBD--$V_LI$-$V_HI$, or

Fc-HBD--$V_HI$-$V_LI$, wherein "$V_LI$" is a light chain variable domain specific for an immune cell antigen;

wherein "$V_HI$" is a heavy chain variable domain specific for the immune cell antigen;

wherein "HBD" is a heparin binding domain comprising the amino acid sequence SEQ ID NO:3;

wherein "-" consists of a peptide linker or a peptide bond;

wherein "--" consists of a peptide linker or a peptide bond; and wherein "Fc" consists of an optional Fc domain of an immunoglobulin; and further wherein $V_HI$ and $V_LI$ form an immune cell antigen binding region, and wherein the immune cell antigen binding region comprises the amino acid sequence SEQ ID NO:1 or SEQ ID NO:2.

5. A single chain antibody, comprising the polypeptide of claim 4, wherein the $V_LI$ and the $V_HI$ have dimerized.

6. An isolated nucleic acid encoding the polypeptide of claim 4.

7. A vector comprising the isolated nucleic acid of claim 6 operably linked to an expression control sequence.

8. An isolated cell comprising the vector of claim 7.

9. A method of treating cancer in a human subject comprising administering to the subject a therapeutically effective amount of one or more of the polypeptides of claim 1.

10. The method of claim 9, further comprising administering to the subject a checkpoint inhibitor.

11. The method of claim 9, wherein the checkpoint inhibitor comprises an anti-PD-1 antibody, anti-PD-L1 antibody, anti-CTLA-4 antibody, or a combination thereof.

* * * * *

SEQUENCE LISTING

<160> NUMBER OF SEQ ID NOS: 3

<210> SEQ ID NO 1
<211> LENGTH: 268
<212> TYPE: PRT
<213> ORGANISM: Artificial Sequence
<220> FEATURE:
<223> OTHER INFORMATION: Synthetic Construct

<400> SEQUENCE: 1

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Gln Val Gln Leu Gln
            20                  25                  30

Glu Ser Gly Ala Glu Leu Ala Arg Pro Gly Ala Ser Val Lys Met Ser
        35                  40                  45

Cys Lys Ala Ser Gly Tyr Thr Phe Thr Arg Tyr Thr Met His Trp Val
    50                  55                  60

Lys Gln Arg Pro Gly Gln Gly Leu Glu Trp Ile Gly Tyr Ile Asn Pro
65                  70                  75                  80

Ser Arg Gly Tyr Thr Asn Tyr Asn Gln Lys Phe Lys Asp Lys Ala Thr
                85                  90                  95

Leu Thr Thr Asp Lys Ser Ser Ser Thr Ala Tyr Met Gln Leu Ser Ser
            100                 105                 110

Leu Thr Ser Glu Asp Ser Ala Val Tyr Tyr Cys Ala Arg Tyr Tyr Asp
        115                 120                 125

Asp His Tyr Cys Leu Asp Tyr Trp Gly Gln Gly Thr Thr Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Leu Thr Gln Ser Pro Ala Ile Met Ser Ala Ser Pro
                165                 170                 175

Gly Glu Lys Val Thr Met Thr Cys Ser Ala Ser Ser Ser Val Ser Tyr
            180                 185                 190

Met Asn Trp Tyr Gln Gln Lys Ser Gly Thr Ser Pro Lys Arg Trp Ile
        195                 200                 205

Tyr Asp Thr Ser Lys Leu Ala Ser Gly Val Pro Ala His Phe Arg Gly
    210                 215                 220

Ser Gly Ser Gly Thr Ser Tyr Ser Leu Thr Ile Ser Gly Met Glu Ala
225                 230                 235                 240

Glu Asp Ala Ala Thr Tyr Tyr Cys Gln Gln Trp Ser Ser Asn Pro Phe
                245                 250                 255

Thr Phe Gly Ser Gly Thr Lys Leu Glu Ile Lys Arg
            260                 265

<210> SEQ ID NO 2
<211> LENGTH: 271
<212> TYPE: PRT
<213> ORGANISM: Artificial Sequence
<220> FEATURE:
<223> OTHER INFORMATION: Synthetic Construct

<400> SEQUENCE: 2

Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Gln Val Gln Leu Gln
            20                  25                  30

```
Gln Ser Gly Thr Glu Leu Val Lys Pro Ala Ser Ser Val Lys Ile Ser
            35                  40                  45

Cys Lys Ala Ser Gly Tyr Thr Ser Thr Ser Asn Tyr Met His Trp Ile
 50                  55                  60

Arg Gln Gln Pro Gly Asn Gly Leu Glu Trp Ile Gly Arg Ile Tyr Pro
 65                  70                  75                  80

Gly Asn Gly Asn Thr Lys Tyr Asn Gln Lys Phe Asp Gly Lys Ala Thr
                    85                  90                  95

Pro Thr Ala Asp Lys Ser Ser Ser Thr Ala Tyr Met Gln Leu Ser Arg
                100                 105                 110

Leu Thr Phe Glu Asp Ser Ala Val Tyr Phe Cys Ala Ser Ala Pro Leu
                115                 120                 125

Asp Tyr Gly Gly His Ile Met Asp Ala Trp Gly Gln Gly Thr Thr Val
                130                 135                 140

Thr Val Ser Ser Gly Gly Gly Gly Ser Gly Gly Gly Gly Ser Gly Gly
145                 150                 155                 160

Gly Gly Ser Asp Ile Gln Leu Thr Gln Ser Pro Ala Phe Leu Ser Ala
                165                 170                 175

Ser Leu Gly Glu Thr Val Ser Ile Glu Cys Leu Gly Ser Glu Asp Ile
                180                 185                 190

Tyr Gly Tyr Leu Ala Trp Tyr Gln Gln Lys Pro Gly Lys Ser Pro Gln
                195                 200                 205

Leu Leu Ile Tyr Val Ala Asn Arg Leu Gln Asp Gly Val Pro Ser Arg
                210                 215                 220

Phe Ser Gly Ser Gly Ser Gly Thr Gln Tyr Ser Leu Lys Ile Ser Gly
225                 230                 235                 240

Met Gln Pro Glu Asp Glu Gly Asp Tyr Tyr Cys Leu Gln Gly Ser Lys
                245                 250                 255

Phe Pro Leu Thr Phe Gly Ser Gly Thr Lys Leu Glu Ile Lys Arg
                260                 265                 270

<210> SEQ ID NO 3
<211> LENGTH: 271
<212> TYPE: PRT
<213> ORGANISM: Artificial Sequence
<220> FEATURE:
<223> OTHER INFORMATION: Synthetic Construct

<400> SEQUENCE: 3

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
                20                  25                  30

Arg Val Arg Val Thr Pro Lys Glu Lys Thr Gly Pro Met Lys Glu Ile
                35                  40                  45

Asn Leu Ala Pro Asp Ser Ser Ser Val Val Val Ser Gly Leu Met Val
 50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
                100                 105                 110

Ser Trp Arg Thr Lys Thr Glu Thr Ile Thr Gly Phe Gln Val Asp Ala
                115                 120                 125
```

-continued

```
Val Pro Ala Asn Gly Gln Thr Pro Ile Gln Arg Thr Ile Lys Pro Asp
    130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
    210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr
            260                 265                 270
```